US012576390B2

(12) United States Patent
    Anashkin

(10) Patent No.:  US 12,576,390 B2
(45) Date of Patent:    Mar. 17, 2026

(54) HYDROCARBONS DEHYDROGENATION CATALYST (VARIANTS)

(71) Applicant: Dmitry Aleksandrovich Anashkin, Kazan (RU)

(72) Inventor: Dmitry Aleksandrovich Anashkin, Kazan (RU)

(73) Assignee: WOLP PTE. LTD., Singapore (SG)

( * ) Notice: Subject to any disclaimer, the term of this patent is extended or adjusted under 35 U.S.C. 154(b) by 238 days.

(21) Appl. No.: 18/290,503

(22) PCT Filed: Jan. 11, 2023

(86) PCT No.: PCT/RU2023/000005
    § 371 (c)(1),
    (2) Date: Nov. 14, 2023

(87) PCT Pub. No.: WO2023/149819
    PCT Pub. Date: Aug. 10, 2023

(65) Prior Publication Data
    US 2024/0139714 A1      May 2, 2024

(30) Foreign Application Priority Data
    Feb. 7, 2022    (RU) ................................ 2022102978

(51) Int. Cl.
    *B01J 21/04*        (2006.01)
    *B01J 23/26*        (2006.01)
    *B01J 35/64*        (2024.01)
    *C07C 5/32*         (2006.01)
(52) U.S. Cl.
    CPC .............. *B01J 21/04* (2013.01); *B01J 23/26* (2013.01); *B01J 35/647* (2024.01); *C07C 5/322* (2013.01); *C07C 2521/04* (2013.01); *C07C 2523/26* (2013.01)

(58) Field of Classification Search
    CPC . B01J 21/04; B01J 23/26; B01J 35/647; B01J 35/70; B01J 37/0207; C07C 5/322; C07C 2521/04; C07C 2523/26; C07C 5/3332
    See application file for complete search history.

(56) References Cited

U.S. PATENT DOCUMENTS

2004/0092391 A1      5/2004   Rokicki et al.
2019/0308172 A1 *   10/2019   Zou ......................... B01J 37/16

FOREIGN PATENT DOCUMENTS

RU          2287366        11/2006
RU          2627664        8/2017
WO      WO2014096628       6/2014

OTHER PUBLICATIONS

Egorova et al. ("Stabilizing effect of α-Cr2O3 on highly active phases and catalytic performance of a chromium alumina catalyst in the process of isobutane dehydrogenation", Molecular Catalysis 509 (2021) 111610). (Year: 2021).*

* cited by examiner

*Primary Examiner* — Ali Z Fadhel
(74) *Attorney, Agent, or Firm* — Aleksandr Smushkovich

(57) ABSTRACT

The claimed solution relates to catalysts for the hydrocarbons dehydrogenation, and particularly relates to a novel catalyst having a structure that makes it possible to provide high olefin selectivity and a high yield of olefins in a dehydrogenation process. The aim of the present solution is to develop a catalyst structure that provides greater selectivity and a higher yield of olefins in hydrocarbons dehydrogenation processes. The effect of the present solution includes providing high catalytic activity and selectivity in hydrocarbons dehydrogenation processes, and expanding the range of products applicable in hydrocarbons dehydrogenation processes.

6 Claims, No Drawings

HYDROCARBONS DEHYDROGENATION CATALYST (VARIANTS)

CROSS-REFERENCE TO RELATED APPLICATIONS

This application is a U.S. national stage application of an international application PCT-RU2023-000005 filed on 11 Jan. 2023, published as WO/2023/149819, which international application claims priority of a Russian Federation patent application RU2022102978 filed on 7 Feb. 2022.

FIELD OF THE INVENTION

The present invention relates generally to the field of catalysts. In particular, the invention relates to chromia-alumina catalysts with a structure that allows to provide high selectivity towards olefins and a high olefins yield in hydrocarbons dehydrogenation processes.

TERMS $D_{50}^{av}$ – pore diameter, at which pore volume fraction with diameter from 0 to $$D_{50}^{av}$$

is 50% from overall catalyst pore volume.

X ($\alpha$-$Cr_2O_3$)—mass fraction of $\alpha$-$Cr_2O_3$ relative to all chromium oxides mass fraction, defined as $$X(\alpha - Cr_2O_3) = \frac{m(\alpha - Cr_2O_3)}{m(Cr_xO_y)}$$

Where m($\alpha$-$Cr_2O_3$)—overall mass fraction of $\alpha$-$Cr_2O_3$ in the catalyst (determined by X-ray phase analysis), m($Cr_xO_y$)—mass fraction of all Chromium oxides in the catalyst MTBE—methyl tert-butyl ether MTAE—methyl tert-amyl ether

BACKGROUND OF THE INVENTION

Olefins are an important raw material for the production of a wide range of bulk chemical products, including rubbers, polyolefins, and high-octane additives for motor fuels (MTBE, MTAE). Catalytic dehydrogenation of hydrocarbons $C_3$-$C_5$ is one of the most significant method for olefins production. In industry, catalytic dehydrogenation of hydrocarbons is carried out using fixed bed, moving bed or fluidized bed reactors. The economic indicators of the catalytic dehydrogenation process are highly sensitive to the properties of the catalysts used; therefore the search for possible ways to optimize catalysts that could provide maximum selectivity maximum yield of the target olefin and simple preparation procedure is an important task.

Despite some environmental issues, chromia-alumina dehydrogenation catalysts are of great importance and widely used in a large-scale technologies such as CATOFIN (R), CATADIENE (R) and SNAMPROGETTI-YARSINTEZ process.

In particular, a method for preparing a catalyst for dehydrogenation of hydrocarbons is disclosed, which involves impregnating the product of thermochemical activation of hydroargillite with solutions of chromium and alkali metal compounds, followed by drying and calcination (Russian Fed. Pat. No. RU2539300). Impregnation and drying occur under the action of microwave radiation with a frequency of 2.45 GHz and a power of 180-2000 W.

Another method of obtaining $C_3$-$C_5$ hydrocarbons dehydrogenation catalyst and alumina support is disclosed in Russian Fed. Pat. No RU2350594. Catalyst has the following composition: $Cr_2O_3$-10-20% mass, $K_2O$-0,1-5% mass, promoter-0,1-5% mass, alumina-balance. The method includes autoclave treatment of product of thermal activation of hydrargillite in the presence of inert gas and/or ammonia and/or carbon dioxide at temperatures from 100 to 300° C. and pressures up to 150 atm to produce suitable catalyst support.

A catalyst for hydrocarbons dehydrogenation and a method of its preparation is disclosed in Russian Fed. Pat. No RU2256499. The support for this catalyst is prepared from a powdered mixture comprising aluminum powder and a bonding component—the product of thermal activation of gibbsite. The mixture is placed in a pressing mold permeable to steam and processed under hydrothermal conditions. After hydrothermal treatment, the resulting granulated product is extracted from the pressing mold, dried, and calcined. The catalyst is prepared by impregnating the carrier granules with an aqueous solution of CrO3, and simultaneously adding soluble salts of modifying additives, sodium and cerium, to the impregnation solution with chromic acid. Catalyst has the following composition after calcination: $Cr_2O_3$-12-25% mass, $Na_2O$-0,2-1% mass, $CeO_2$-0,1-2% mass.

A catalyst for the hydrocarbons dehydrogenation and a method of its preparation is disclosed in Russian Fed. Pat. No. RU2287366 herein chosen as a prototype (the closest related art). The catalyst contains alumina oxides, chromium oxides and promoters. The catalyst is prepared by impregnating aluminum compound of the formula $Al_2O_3 \cdot n$ H2O, where n=0.3-1.5, with an aqueous solution of boron and/or silicon compounds, followed by drying impregnation of alkali and/or alkaline earth metal compounds, chromium, and a modifying component. The catalyst has overall pore volume of 0,15-0.4 ml/g.

The common drawbacks of the described above methods are low olefin yield and low selectivity in the dehydrogenation process and, in particular, the complex preparation procedures. The object of the present invention is to develop a catalyst with an optimized structure that allows to achieve increased olefins yield and selectivity in hydrocarbons dehydrogenation processes.

SUMMARY OF THE INVENTION

The object of the present invention is achieved by optimizing alumina-chromia catalyst porous structure (obtaining optimal $$D_{50}^{av}$$

3 value) and $\alpha$-Cr$_2$O$_3$ mass fraction relative to all chromium oxides mass fraction (X ($\alpha$-Cr2O3)). It was found that the optimal value of average pore diameter $$D_{50}^{av}$$

should be within the range of 12-25 nm for the catalysts operating in fluidized bed conditions (first variant), and within the range of 15-100 nm for the catalysts operating in fixed bed conditions (second variant) to avoid mass transfer limitations and ensure a high yield of olefins and selectivity. The optimal value of X ($\alpha$-Cr2O3) for fixed and fluidized bed catalysts should be within the range of 0.3-6% mass.

DETAILED DESCRIPTION OF THE INVENTION

The formation of the main reaction products (olefins, dienes, cracking products, and coke) in the process of light hydrocarbons dehydrogenation over chromia-alumina catalysts mainly occurs through the following sequential stages:

Hydrocarbon→target olefin and/or diene→cracking products, coke.

The target dehydrogenation products (olefins and dienes) undergo cracking at the catalyst surface and require rapid removal from the catalyst's porous space to ensure maximum process selectivity and product yield. The larger is catalyst pores, the more effective is mass transfer in the catalyst particles and the more is olefins selectivity. But very large pores have low specific surface resulting to low catalyst activity and, consequently low product yield. So, to achieve maximum activity and maximum selectivity the optimal catalyst pore size depending on the catalyst particle size and process kinetics is required.

It was discovered in our investigations, that pores with a diameter<10 nm in our chromia-alumina catalysts provide the highest catalytic activity, both in dehydrogenation reactions and in side reactions such as cracking and coke formation. Meanwhile, pores with a diameter>25 nm facilitate the effective transport of hydrocarbons within the catalyst grains, but their contribution to the conversion of hydrocarbons is relatively low.

Therefore, increasing the fraction of pores<10 nm in the catalysts and consequently reducing the value of $$D_{50}^{av}$$

below optimum leads to an increase of hydrocarbons conversion and decrease of selectivity. Conversely, reducing the fraction of small pores<10 nm by increasing the fraction of larger-diameter pores, and consequently increasing the value of $$D_{50}^{av}$$

above the optimal level, results in reduced catalytic activity and a decline in hydrocarbons conversion and olefins yield.

It was discovered that to obtain the object of the present invention the optimal value of $$D_{50}^{av}$$

should be within the range of 12-25 nm for the chromia-alumina catalysts operating in fluidized bed conditions, and within the range of 15-100 nm for chromia-alumina catalysts operating in fixed bed conditions. Fluidized bed dehydrogenation catalysts have relatively small average particle diameters (20-200 μm) compared to fixed bed catalysts (1-6 mm) and therefore require a smaller value of $$D_{50}^{av}$$

to reduce mass transfer limitations.

The mass fraction of $\alpha$-Cr$_2$O$_3$(X ($\alpha$-Cr$_2$O$_3$)) relative to the total chromium oxides mass fraction was found to be one more significant parameter influencing catalytic performance of chromia-alumina catalysts. It is known that in chromia-alumina catalysts active sites are represented primarily by Cr$_2$O$_3$ which could be finely dispersed (X-ray amorphous Cr$_2$O$_3$) and/or crystallized as $\alpha$-Cr$_2$O$_3$/which can be well-defined using X-ray phase analysis (XPA).

It is known that finely dispersed X-ray amorphous Cr$_2$O$_3$ exhibits the highest activity and selectivity in the hydrocarbons dehydrogenation reaction, while $\alpha$-Cr$_2$O$_3$ displays lower activity and selectivity, but much higher catalytic stability compared to amorphous Cr$_2$O$_3$. So, the presence of $\alpha$-Cr$_2$O$_3$ at the catalyst surface could compensate quick losses of activity of amorphous Cr$_2$O$_3$ and optimum content of $\alpha$-Cr$_2$O$_3$ allows compensating for the loss of highly active amorphous without losses of olefins selectivity and yield. It was discovered that to achieve a high yield of olefins, high selectivity, and stability of the chromia-alumina catalyst, the optimal value of X ($\alpha$-Cr2O3), at which the catalyst's activity and selectivity parameters do not deteriorate, falls within the range of 0.3-6% by mass. This value was found to be the same for both fixed bed and fluidized bed catalysts.

So, the object of the present invention was achieved by the following ways:

1. By adjusting the value of average pore diameter $$D_{50}^{av}$$

within the range of 12-25 nm and the value of X ($\alpha$-Cr2O3)) within the range of 0,3-6% mass. for a fluidized bed catalyst for hydrocarbons dehydrogenation (first variant). At least one alkali metal and at least two Group IV elements were used as promoters.

2. By adjusting the value of average pore diameter $$D_{50}^{av}$$

within the range of 15-100 nm and the value of X ($\alpha$-Cr2O3)) within the range of 0,3-6% mass. for a fixed bed catalyst for hydrocarbons dehydrogenation (second variant). At least one alkali metal and at least two Group IV elements were used as promoters.

The specified value of the average pore diameter $$D_{50}^{av}$$

in the catalyst was achieved by selecting the method for preparing the support and calcination conditions. The specified value of X (α-Cr2O3) in the catalyst was achieved by selecting the chemical composition of the catalyst and its final calcination conditions, which are determining factor in the formation of the porous structure of the support and catalyst. During calcination processes such as sintering, recrystallization, and changes in pore size distribution take place. These processes are accelerated with increasing temperature. Calcination at relatively low temperatures results in the formation of small pores while increasing the calcination temperature leads to larger pore sizes.

Caclination temperature and conditions also influence on $Cr_2O_3$ dispersion. Increased calcination temperature leads to consolidation of fine $Cr_2O_3$ particles and formation of α-Cr2O3.

The catalysts in the present invention were prepared as follows.

1. Fluid Bed Catalyst (First Variant).

Powdered gibbsite was calcined at the temperature up to 850 C to provide alumina support with $$D_{50}^{av}$$

value close to given value. The obtained support was impregnated with the aqueous solution of precursors of active components and dried at a temperature of 150-200° C. during 2 hours. The catalyst was obtained by calcination of the impregnated and dried support at the temperatures that ensure both the complete decomposition of precursor compounds and the final formation of the optimal $$D_{50}^{av}$$

and (X (α-Cr2O3)). Catalyst had particle size of 20-200 mkm and was designed for operation in fluidized bed conditions.

2. Fixed Bed Catalyst (Second Variant)

The support was prepared by mixing powdered alumina with pseudoboehmite, followed by plasticization of the resulting mixture with nitric acid solution and extrusion of the plastic mass into granules. The extruded granules were dried and calcined under conditions that provide a pore size close to the specified $$D_{50}^{av}.$$

The obtained support was impregnated with the aqueous solution of precursors of active components and dried at a temperature of 150-200° C. The catalyst was obtained by calcination of the impregnated and dried support at the temperatures that ensure both the complete decomposition of precursor compounds and the final formation of the optimal $$D_{50}^{av}$$

and (X (α-Cr2O3)). Catalyst had particle size of 1-8 mm and was designed for operation in fixed bed conditions.

Prepared catalysts (first and second variants) contained aluminum oxides, chromium oxides and promoters. Alkali metals and Group IV elements were used as promoters to optimize the acidity of active centers and to reduce by-products formation.

The catalytic properties of the prepared catalyst samples were studied in a laboratory setup using fixed and fluidized bed reactors and sequence of reaction-regeneration stages. The reaction temperature varied in the range of 540-580° C., the reaction pressure was 0,1-0.12 MPa, and the reaction time ranged from 15 to 30 minutes. Gas analysis at the reactor outlet was carried out at the 13th minute from the moment of hydrocarbon feed. After reaction stage the catalyst was regenerated with oxygen-containing gas (primarily by air) during 25-50 min at a temperature of 600-720° C., regeneration pressure was 0.1 MPa.

The pore size distribution and $$D_{50}^{av}$$

were investigated:
  1. For the fluidized bed catalysts by using the BJH method based on the nitrogen adsorption isotherm on an ASAP-2020MP instrument.
  2. For the fixed bed catalysts by using Autopore IV 9510 mercury intrusion porosimeter.

The content of α-Cr2O3 in the catalysts was determined by X-ray diffraction analysis using the SHIMADZU XRD-7000 instrument with an absolute calibration method based on the determined phase (α-Cr2O3).

The following examples illustrate and explain the present invention, but are not to be taken as limiting the present invention in any regard. Parts and percentages are indicated by weight unless otherwise designated Examples show, that hydrocarbons dehydrogenation catalysts (for operation at fixed bed and fluidized bed conditions) having optimal value $$D_{50}^{av}$$

and optimal value X (α-Cr2O3)) provide highest olefins yield and selectivity.

Example 1

Powdered gibbsite with particle sizes of 20-200 μm is calcined at a temperature of 800-850° C. to obtain an alumina catalyst support.

The support is impregnated by pore volume with a solution containing water-soluble compounds of Na, K, Cr, Sn, Ti, Zr in quantities necessary to obtain a catalyst with the following composition:
  $Cr_2O_3$—17.8%
  $K_2O$—2.5%.
  $Na_2O$—0.23%

$SnO_2$—1.2%.

$TiO_2$—0.2%

$ZrO_2$—1.4%

$Al_2O_3$—up to 100% balance.

The impregnated support is dried at 100° C. for 4 hours, then calcined at 760-800° C. for 12 hours. The resulting catalyst has an average pore diameter $$(D_{50}^{av})$$

of 16 nm and X (α-Cr2O3)) of 1%.

Example 2

The catalyst is prepared as described in Example 1, with the difference being that to obtain the catalyst support, gibbsite powder is calcined at a temperature of 820-850° C. in a steam flow. The resulting catalyst has an average pore diameter $$(D_{50}^{av})$$

of 30 nm and X (α-Cr2O3)) of 1%.

Example 3

The catalyst is prepared as described in Example 1, with the difference being that to obtain the catalyst support, gibbsite powder is calcined at 450-550° C. The resulting catalyst has an average pore diameter $$(D_{50}^{av})$$

of 30 nm and X (α-Cr2O3)) of 1%.

Example 4

The catalyst is prepared as described in Example 1, with the difference being that the support is impregnated by pore volume with a solution containing water-soluble compounds of Na, K, Cr, Sn, Ti, Zr in quantities necessary to obtain a catalyst with the following composition:

Cr2O3—22%

K2O—2.5%

Na2O—0.23%

SnO2—1.2%

TiO2—0.2%

ZrO2—1.4%

Al2O3—up to 100% balance.

The impregnated support is dried at 100° C. for 4 hours, then calcined at 920° C. for 2-12 hours. The resulting catalyst has an average pore diameter $$(D_{50}^{av})$$

of 16 nm and X (α-Cr2O3)) of 10%.

Example 5

The catalyst is prepared as described in Example 1, with the difference being that the support is impregnated by pore volume with a solution containing water-soluble compounds of Na, K, Cr, Sn, Ti in quantities necessary to obtain a catalyst with the following composition:

Cr2O3—14.6%

K2O—2.5%

Na2O—0.23%

SnO2—1.2%

TiO2—0.4%

ZrO2—1.4%

Al2O3—up to 100% balance.

The impregnated support is dried at 100° C. for 4 hours, then calcined at 680° C. for 12-18 hours. The resulting catalyst has an average pore diameter $$(D_{50}^{av})$$

of 16 nm and X (α-Cr2O3)) of 0,1%.

Example 6

Powdered gibbsite with particle sizes of 40-80 μm is calcined at a temperature of 800-850° C. to obtain powdered aluminum oxide. The obtained aluminum oxide is mixed with pseudoboehmite (PB) powder and wood flour in a mass ratio of $Al_2O_3$:PB:flour=1:1:0.05, and a nitric acid solution is added and stirred for 2 hours to obtain a plastic mass. This mass is then extruded to obtain cylindrical pellets with a diameter of 4.5 mm. The resulting pellets are calcined at 820-850° C. in an air stream to obtain the catalyst support. The obtained support is impregnated by pore volume with a solution containing water-soluble compounds of Na, K, Cr, Sn, Ti, Zr in quantities necessary to obtain a catalyst with the following composition:

Cr2O3—17.8%

K2O—2.5%

Na2O—0.23%

SnO2—1.2%

TiO2—0.2%

ZrO2—1.4%

Al2O3—up to 100% balance.

The impregnated support is dried at 100° C. for 4 hours, then calcined at 760-800° C. The resulting catalyst has an average pore diameter $$(D_{50}^{av})$$

of 35 nm and X (α-Cr2O3)) of 1%.

Example 7

Gibbsite powder with particle sizes of 40-80 μm is calcined at a temperature of 800-850° C. to obtain powdered aluminum oxide. The obtained aluminum oxide is mixed with pseudoboehmite (PB) powder and wood flour in a mass ratio of Al2O3:PB:flour=1:1:0.12, and a nitric acid solution is added. The mixture is stirred for 2 hours to obtain a plastic mass. The following catalyst preparation procedure is the same as in example 6. The resulting catalyst has an average pore diameter $$(D_{50}^{av})$$

of 120 nm and X (α-Cr2O3)) of 1%.

Example 8

Gibbsite powder with particle sizes of 20-40 µm is calcined at a temperature of 800-850° C. to obtain powdered aluminum oxide. The obtained aluminum oxide is mixed with pseudoboehmite (PB) powder in a mass ratio of Al2O3: PB=1:3, and a nitric acid solution is added. The mixture is stirred for 2 hours to obtain a plastic mass. The following catalyst preparation procedure is the same as in example 6. The resulting catalyst has an average pore diameter $$(D_{50}^{av})$$

of 10 nm and X ($\alpha$-Cr2O3)) of 1%.

As it's seen from the Table 1 below, fluidized bed catalyst (example 1) having optimal values of $$D_{50}^{av}$$

and X ($\alpha$-Cr2O3) shows the highest olefin yield and selectivity compared to examples 2,3,4,5 with the $$D_{50}^{av}$$

and X ($\alpha$-Cr2O3) being out of optimal range. The fixed bed catalyst (example 6) having optimal values of $$D_{50}^{av}$$

shows superior olefin yield and selectivity prior to examples 7 and 8. X ($\alpha$-Cr2O3) for all examples (6,7,8) was within optimal value range.

TABLE 1

Physical and catalytic properties of the catalysts

| Example | $D_{50}^{av}$, nm | X ($\alpha$-Cr$_2$O$_3$). | Reactor type | Feed | Olefin yield, % | Olefin selectivity, % |
|---|---|---|---|---|---|---|
| 1 | 16 | 1 | Fluid bed | isobutane | 53 | 90 |
|  |  |  |  | propane | 42 | 92 |
| 2 | 30 | 1 | Fluid bed | isobutane | 44 | 91 |
| 3 | 6 | 1 | Fluid bed | isobutane | 50 | 85 |

TABLE 1-continued

Physical and catalytic properties of the catalysts

| Example | $D_{50}^{av}$, nm | X ($\alpha$-Cr$_2$O$_3$). | Reactor type | Feed | Olefin yield, % | Olefin selectivity, % |
|---|---|---|---|---|---|---|
| 4 | 16 | 10 | Fluid bed | isobutane | 49 | 86 |
| 5 | 16 | 0.1 | Fluid bed | isobutane | 48 | 90 |
| 6 | 35 | 1 | Fixed bed | isobutane | 63 | 96.5 |
| 7 | 120 | 1 | Fixed bed | isobutane | 54 | 96 |
| 8 | 10 | 1 | Fixed bed | isobutane | 57 | 85 |
| Prototype |  |  | Fluid bed | isobutane | 51.9 | 85.9 |
|  |  |  | Fixed bed | isobutane | 48 | 85.7 |

The invention claimed is:

1. A catalyst for dehydrogenation of hydrocarbons at fluidized bed conditions, comprising aluminium oxides, chromium oxides, and promoters, wherein the average catalyst pore diameter $$(D_{50}^{av})$$

is 12-25 nm, and the mass fraction of $\alpha$-Cr$_2$O$_3$ in the catalyst (X ($\alpha$-Cr$_2$O$_3$)) is 0.3-6% of mass fraction of all chromium oxides in the catalyst.

2. The catalyst according to claim 1 comprising at least one alkali metal and at least two Group IV elements as promoters.

3. A catalyst for dehydrogenation of hydrocarbons at fixed bed conditions, comprising aluminium oxides, chromium oxides, and promoters, wherein the average catalyst pore diameter $$(D_{50}^{av})$$

is 15-100 nm, and the mass fraction of $\alpha$-Cr$_2$O$_3$ in the catalyst X ($\alpha$-Cr$_2$O$_3$) is 0.3-6% of mass fraction of all chromium oxides in the catalyst.

4. The catalyst according to claim 3, comprising at least one alkali metal and at least two Group IV elements as promoters.

5. The catalyst according to claim 1, wherein said aluminium oxides are obtained by gibbsite calcination at 800-850 C.

6. The catalyst according to claim 3, wherein at least part of said aluminium oxides are obtained by gibbsite calcination at 800-850 C.

* * * * *